United States Patent [19]

Oka et al.

[11] Patent Number: 4,897,468

[45] Date of Patent: Jan. 30, 1990

[54] IMMOBILIZATION OF PEPTIDE-CONTAINING COMPOUNDS ON METAL HYDROXIDE GELS

[75] Inventors: Shotaro Oka, Muko; Shu Tahara, Nagaokakyo; Hiroyoshi Minakuchi; Hajime Karatani, both of Kyoto, all of Japan

[73] Assignee: Shimadzu Corporation, Kyoto, Japan

[21] Appl. No.: 243,156

[22] Filed: Sep. 9, 1988

Related U.S. Application Data

[63] Continuation of Ser. No. 1,358, Jan. 8, 1987, abandoned, which is a continuation of Ser. No. 833,843, Feb. 26, 1986, abandoned, which is a continuation of Ser. No. 517,060, Jul. 25, 1983, abandoned.

[30] Foreign Application Priority Data

Dec. 29, 1981 [JP]  Japan .................................. 56-230159
Jul. 29, 1982 [JP]  Japan .................................. 57-133055
Mar. 31, 1983 [JP]  Japan .................................. 58-57508

[51] Int. Cl.$^4$ ...................... C07K 17/14; C12N 11/14; G01N 33/551; G01N 33/552
[52] U.S. Cl. .................................... 530/811; 435/176; 436/524; 436/527
[58] Field of Search ............... 435/174, 176, 177, 186, 435/182, 288; 530/810, 811, 812; 436/524, 527

[56] References Cited

U.S. PATENT DOCUMENTS

| 3,948,806 | 6/1972 | Miller | 435/176 |
| 4,148,689 | 4/1979 | Hino et al. | 435/182 |
| 4,243,692 | 1/1981 | Scholze et al. | 435/176 |
| 4,461,832 | 7/1984 | Tschang et al. | 435/176 |

*Primary Examiner*—David M. Naff
*Attorney, Agent, or Firm*—Bryan, Cave, McPheeters & McRoberts

[57] ABSTRACT

Peptide-containing compounds such as enzymes, antibodies and antigens are immobilized on metal hydroxy gels formed by hydrolysis of metal alkoxides in an aqueous solvent while evaporating off the solvent. Preferably, hydrogen fluoride is present in the solvent during hydrolysis to provide a fluoride-substituted metal hydroxy gel. Water containing lower alcohol is a preferred solvent. The gel is treated with a coupling agent and a peptide-containing compound is chemically bonded to the gel.

10 Claims, 5 Drawing Sheets

IMMOBILIZATION OF PEPTIDE-CONTAINING COMPOUNDS ON METAL HYDROXIDE GELS

This application is a continuation of application Ser. No. 001,358, filed Jan. 8, 1987, now abandoned, which is a continuation of application Ser. No. 833,843, filed Feb. 26, 1986, now abandoned, which is a continuation of application Ser. No. 517,060, filed July 25, 1983, now abandoned.

BACKGROUND OF THE INVENTION

1. Field of the Invention

The present invention relates to a bioreactor and a process for production thereof and, more particularly a bioreactor suited for use of analysis, diagnosis and synthesis which comprises immobilizing a peptide-containing compound such as a biocatalyst, etc. to a specific carrier, as well as a process for production thereof.

2. Description of the Prior Art

Recently, immobilized glasses which comprise immobilized peptide-containing compounds such as an enzyme or the like on a glass carrier have been employed as bioreactors for use in analysis, diagnosis or synthesis. As a process for producing these bioreactors, a process which comprises treating the surface of a $SiO_2$ type glass previously obtained by a fusion technique with an alkali to form hydroxy groups therein, introducing, e.g., aminoalkyl groups, into the hydroxy group and then immobilizing an enzyme or the like, is known and has been reduced to practical use. To introduce functional groups such as the aforesaid aminoalkyl groups, a method using various silane coupling agents is known.

In the prior art process, however, a step of forming hydroxy groups at the glass surface was required. In addition, the amount of the hydroxy group per unit area which could be formed at this step was limited and an amount of the peptide-containing compound to be immobilized was also limited. It was thus difficult to obtain bioreactors having an increased amount of the peptide-containing compound and having high activity.

The present invention has been accomplished, attempting to eliminate the foregoing problems.

On the other hand, a process for preparing metal oxide glasses which comprises hydrolyzing metal alkoxides as raw materials and treating the resulting glass-like gels at high temperatures is known in the field of glass production, in particular in the field of optical glass production.

The present inventors have found that glass-like gels formed by hydrolyzing metal alkoxides under mild conditions are useful as carriers for immobilizing peptide-containing compounds. Bioreactors can thus be easily obtained incorporating increased amounts of the peptide-containing compounds per unit carrier, in accordance with the present invention.

SUMMARY OF THE INVENTION

According to the present invention, bioreactors which comprise using as carriers glass-like gels comprising metal hydroxide compounds formed by hydrolysis of metal alkoxides and/or condensation products thereof or derivatives thereof obtained by substituting a part of these hydroxy groups with fluorine atoms and immobilizing peptide-containing compounds thereto, as well as a process for production of the bioreactors, are provided.

DESCRIPTION OF THE PREFERRED EMBODIMENTS

As metal alkoxides used in the present invention, various metal alkoxides known in the field of glass production or ceramic production can be employed. Specific examples of the metal alkoxides include lower alkoxysilanes, lower alkoxytitaniums, lower alkoxyaluminums, lower alkoxyvanadiums, lower alkoxy sodiums, etc. such as $Si(OCH_3)_4$, $Si(OC_2H_5)_4$, $Ti(OC_3H_7)_4$, $V(OC_2H_5)_3$, $Al(OC_3H_7)_3$, $NaOCH_3$, etc. of these, it is generally preferred to use lower alkoxysilanes. A mixture of two or more compounds thereof can also be employed.

The bioreactors of the present invention are characterized in that glass-like gels obtained by hydrolysis of the aforesaid metal alkoxides are employed as carriers for immobilization. Furthermore, the term "bioreactor" as used herein means a peptide-containing compound immobilized material, which may be suitably formed on a supporting substrate.

In the case of using, e.g., lower alkoxy silanes, it is generally appropriate that the hydrolysis of the lower alkoxy silanes be carried out in an aqueous solvent in an acidic system under mild conditions. In this case, it is preferred that the hydrolysis proceed while evaporating the solvent off and avoiding elevation of the temperature insofar as possible such that glass-like gels are formed while preventing a high degree of condensation of the metal hydroxide. In this case, it is appropriate to use a volatile hydrophilic solvent as the aqueous solvent. For example, water-containing lower alcohols such as water-containing methanol, water-containing ethanol, etc. are advantageously employed. In some instances the water need not be contained in the solvent since the water may be supplied from the atmosphere. It is also possible to effect the hydrolysis in water alone; in this case, however, there is a danger that the hydrolysis might proceed vigorously and render the system heterogeneous and such is disadvantageous for drying the gels.

It is appropriate that the pH of the solvent be generally adjusted to an acidic area (pH of about 1 to about 3), generally by adding small quantities of inorganic acids such as hydrochloric acid, etc. The glass-like gel used in the present invention is usually isolated by allowing the system to stand in the air, after adding a metal alkoxide in such an aqueous solvent and thoroughly mixing them at room temperature with stirring, to subject the water and the hydrophilic solvent to natural drying.

The thus obtained glass-like gels, particularly gels formed using alkoxy silanes, are provided for practical use. Heat treatment at temperatures of about 100 to about 300° C. for several hours is preferred for removing remaining unreacted substances and impurities, etc. and improving the strength of the carrier to hold its shape per se. However, if the temperature of the heat treatment exceeds about 300° C. (e.g., about 500° C.), siloxane bonds increase within the glass-like gels and cause high degree of condensation so that the amount of hydroxy groups decrease. This is not preferred. with a heat treatment at about 300° C., silanol groups are hardly converted into siloxane bonds, so that the decrease in the activity of the gel is hardly appreciated.

The thus obtained glass-like gels are employed as carriers by immobilizing peptide-containing compounds thereto, as they are or after they are shaped into a desired form (a plate-like, spherical or powdery form), in an appropriate manner. If the glass-like gels are formed in a layer on the inner surface of a glass tube or a stainless tube, a solution of the metal alkoxide in an aqueous solvent is coated onto the inner surface of the tube followed by hydrolysis as it is.

Coupling agents are usually reacted with the glass-like gels and peptide-containing compounds are immobilized on the resulting reaction product; thus, the bioreactors of the present invention are obtained.

Examples of the aforesaid peptide-containing compounds include biocatalysts such as enzymes, etc., antigens, antibodies, and the like.

Specific examples are enzymes, such as glucose oxidase (GOD), cholesterol oxidase (CO), acyl CoA oxidase (ACO), 3-$\alpha$-hydroxysteroid dehydrogenase (3$\alpha$-HSD), glucose-6-phosphate dehydrogenase (G-6-PDH), glutamate-1-dehydrogenase (GlDH), creatininase, uricase, peroxidase, hexokinase (HK), urease, chloesterol esterase (CE), acyl CoA synthetase (ACS), etc.; antigens such as immunoglobulins, $\alpha$-fetoprotein, haptoglobin, HBs etc., and antibodies such as $\alpha_1$-fetoprotein, $\gamma$-globulin, etc.

As the coupling agents described above, silane coupling agents containing functional groups such as an amino group, a thiol group, an epoxy group, etc. which are conventional in the art can be employed, Specific examples include $\gamma$-amino-propyltriethoxysilane, $\gamma$-chloropropyl trimethoxysilane, vinyltriethoxysilane, $\gamma$-glycidoxypropyl trimethoxysilane, N-$\beta$-(aminoethyl-$\gamma$-aminopropyl trimethoxysilane, etc. Cyanogen bromide can also be employed as the coupling agent. The coupling agents are generally bound to the hydroxy groups of the glass-like gels prior to immobilization. These coupling agents serve to immobilize the peptide-containing compounds by introducing functional groups into the gels.

Reaction with the silane coupling agents is carried out under conditions known in the art. For example, when using $\gamma$-aminopropyltriethoxysilane, the coupling agent is dissolved in water to about a 10% aqeuous solution. After adjusting the pH to 3 to 5, the gels described above or shaped gels, which were completely dried, are added to the solution and mixed with heating for several hours. Thereafter to complete the reaction, the mixture is washed with water to remove any unreacted coupling agent.

The binding of the peptide-containing compounds is generally accomplished by utilizing the functional groups contained in the coupling agent described above. For example, in case that the glass-like gels having introduced therein many aminoalkyl groups through ester bonds at the hydroxy groups thereof using $\gamma$-aminopropyl triethoxysilane as the coupling agent are employed, Schiff's bases having an aldehyde group is introduced into the aminoalkyl group described above using glutaraldehyde and an enzyme or the like is contacted therewith to form an additional Schiff's base between the aldehyde group and the amino group of the enzyme or the like, whereby immobilization is effected. In addition, immobilization can also be effected by diazotizing the aminoalkyl group, introducing an aromatic amino group thereto and immobilizing the peptide-containing compound thereon. Further, the immobilization can also be effected by directly forming a peptide bond between the aminoalkyl group and the peptide-containing compound using carbodiimide. The immobilization process used depends upon kind of the peptide-containing compound being immobilized. Enzymes or the like can also be immobilized directly to the coupling group or after appropriately modifying the coupling group, in a similar manner to when other coupling agents are employed.

The bioreactors of the present invention employed as carriers are characterized in that the glass-like gels obtained do not require any heat treatment at high temperatures or introducing hydroxy groups during immobilization. Accordingly, the present invention has greatly reduced costs as compared to the prior art. Further, the bioreactors of the present invention have higher activity than those of the prior art.

The high activity of the bioreactors is explained as follows. That is, the bioreactors of the present invention are characterized by the use of the glass-like gels comprising metal hydroxide compounds and/or condensation products thereof (particularly low degree condensation products) as carriers. When, e.g., $Si(OC_2H_5)_4$ as the metal alkoxide, a glass-like gel is obtained, which gel comprises $Si(OH)_4$ which is a hydrolysate of Si-$(OC_2H_5)_4$ or its low degree condensation product. For this reason, the carrier according to the invention contains many hydroxy groups as compared with a carrier using glass oxide obtained by treatment with an alkali and then the carrier of the invention has a market increase in the amount of peptide-containing compound which can be immobilized; it is thus believed that the carrier would have increased activity as a bioreactor.

When a small quantity of hydrogen fluoride is contained in the aqueous solvent upon the aforesaid hydrolysis, it has also be found that a carrier having a further increased capability for immobilization can be obtained.

By such treatment with hydrogen fluoride, gelation is accelerated and at the same time, part of the hydroxy groups in the metal hydroxide compounds and/or condensation products thereof, which are the hydrolysis products of the metal alkoxides, is substituted with fluorine atoms thus these glass-like gels have fluorine atoms chemically bound thereto. In this instance, it is necessary to introduce a small quantity of fluorine atoms for the substitution and introduction. About 0.05 to about 1.0 mol is appropriate when expressed as a mole ratio to the raw metal alkoxide (1 mol) and about 0.2 mol is most preferred. With 0.05 mol or less, the effect due to the introduction of fluorine atoms is insufficient and such is not preferred. When the molar ratio exceeds 1.0 mol, the degree of substitution of the hydroxy groups in the metal hydroxide compounds and/or condensation products thereof is excessive and the number of the hydroxy groups capable of participating in the subsequent reaction is substantially decreased; such is thus not preferred. The gels obtained by the hydrolysis of the metal alkoxides, part of which is substituted with fluorine, provide an increased capability of immobilizing the peptide-containing compounds, as compared with the gels in which no fluorine substitution is made. Ultra strong acids which generate hydrogen fluoride can also be used in place of hydrogen fluoride. The glass-like gels having fluorine atoms are per se novel compounds and useful as a carrier for various uses.

As is shown in formula (I) below:

(I)

the effect due to the introduction of fluorine atom is believed to be that the degree of polarization in the hydroxy groups in the silanol adjacent thereto is enlarged because of an electrophilic induction effect of the fluorine atom which has been introduced in a small quantity into the metal hydroxide compound or a condensation product thereof. Thus, the hydrogen atom would become active and the reactivity would be more increased. Further, a microsopic observation indicates that the glass-like gels obtained in the presence of hydrogen fluoride upon hydrolysis are highly porous. It is also believed that an effect of increasing surface areas because of high porosity would also contribute to the increased capability of immobilizing the peptide-containing compound.

In the case of making hydrogen fluoride co-present, it is preferred that a small quantity (0.05 to 1.0 mol) of hydrogen fluoride is added to an aqueous medium containing the metal alkoxide and, the formed alcohol, solvent, inorganic acid and unreacted hydrogen fluoride are allowed to evaporate off, while heating at about 80 to about 100° C. and the formed gels are thoroughly dried at about 300° C.

It has also been found that, by accelerating the hydrolysis of the metal alkoxide in a dispersed state obtained by adding a solution of the metal alkoxide and hydrogen fluoride in a aqueous solvent to a liquid hot medium incompatible but dispersible with the solution, spherical glass-like gels are obtained in good efficiency. In this case, hydrogen fluoride serves in the formation of spherical, particularly finely spherical glass-like gels by effectively promoting the hydrolysis per se, in addition to the effect described above. As a small quantity of hydrogen fluoride, it is appropriate to employ 0.1 to 1 mol per 1 mol of the metal alkoxide. Specific examples of liquid hot media which can be employed include hydrocarbon oils such as fluid paraffin, mineral oils, etc.; polyethylene glycol, polypropylene glycol, etc. In addition, various liquids such as synthetic oils, plant oils, etc. can also be employed. Dispersion in a liquid hot medium is generally effected by adding at once followed by stirring. In this case, it is preferred that a volume ratio for mixing the hydrogen fluoride-containing solution with the liquid hot medium be adjusted such that the former be not greater than 1/10 the later. In this ratio spherical glass-like gels can be prepared in a yield of almost 100%. Further it is appropriate that the temperature of the liquid hot medium be set generally at 50 to 200° C. When using, e.g., alkoxy silanes, the temperature of about 80° C. is preferred. Dispersion in this medium is appropriately carried out generally by spraying of the solution described above.

By the dispersion in such a hot medium, the hydrolysis of the metal alkoxide vigorously proceeds so that dispersed grains are converted into gels in several ten minutes and glass-like gels of a spherical form are obtained in a dispersed state. Further, the depersion may be performed by spraying a solution of the metal alkoxide and hydrogen fluoride in an aqueous solvent, in a gaseous hot medium such as a hot air or nitrogen stream.

Particle sizes of the thus formed spherical glass-like gels greatly varies depending upon the viscosity of the metal alkoxide solution; in addition, the particle size also varies depending upon, e.g., the viscosity (temperature) of the liquid hot medium (there is a tendency that when the temperature of the liquid hot medium is low ant the viscosity is relatively high, the particle size becomes large; when the temperature is high and the viscosity is relatively low, the particle size becomes small). Further, the particle size also varies more or less depending upon the time period required for dispersion and a dispersed state. However, by controlling the various conditions it is possible to obtain gels of desired particle sizes such as; gels having a particle size ranging from a large diameter of a mm order to a fine diameter of a μm By immobilizing the peptide-containing compound to the fluorine-treated glass-like gels using the coupling agent as previously described the bioreactors of the present invention can be obtained. In bioreactors containing fluorine, the amount of the peptide-containing compound immobilized is increased and the activity is increased, as compared to the bioreactors using as carriers the glass-like gels containing no fluorine.

Hereafter the present invention will be described with reference to the examples.

EXAMPLE 1

Preparation of Glass-like Gel: Step 1

A mixture (pH 1) of 10 g of tetraethoxysilane Si(OC$_2$H$_5$)$_4$, 10 ml of ethanol, 3.8 ml of water and 1.4 ml of hydrochloric acid (1N) was mixed at room temperature for about 1 hour with stirring until the system became homogeneous. The mixture was allowed to stand in the air for about 4 days to allow hydrolysis and the evaporation of water and ethanol. Then, the system was dried at about 120° C. to obtain a glass-like gel of Si(OH)$_4$ type. (Aminoalkylation: Step 2)

The gel obtained at Step 1 was ground in a glass mortar and passed through sieves to obtain beads having means grain sizes of 60/80, 80/120 and 120/200.

45 ml of a 5 wt. % γ-aminopropyltriethoxysilane aqueous solution was adjusted to pH 3.5 with 5N hydrochloric acid, to and 5 g each of the aforesaid beads-like gel was added. The system was again adjusted to pH 3.5. The mixture was charged in a four-necked flask equipped with a stirred, a thermometer and a Dimroth's funnel. While maintaining the temperature at 75° C. in a water bath, the reaction was carried out for 3 hours while vigorously stirring. After completion of the reaction, the beads were moved to a suction membrane filter to remove the unreacted γ-aminopropyltriethoxysilane with 1l of distilled water. Then, the system was dried in a desicator to obtain three kinds of aminoalkylated glass-like gels having different grain sizes. The aminoalkylated gels are stored in a desicator.

Immobilization of enzyme: Step 3

The above-described aminoalkylated gels (beads-like) were immersed in each of a phosphate buffer solution (pH 7.0, 0.1M) of bifunctional glutaraldehyde (2.5 wt. %). While reducing the pressure with an aspirator, the reaction was carried out for about 30 minutes with stirring. Subsequently, the reaction was carried out for about 30 minutes under normal pressure. The reaction temperature was 25° C. The reaction mixture was thoroughly washed with a phosphate buffer solution (0.1M, pH 7.0) followed by drying. By this treatment, a Schiff's base containing an aldehyde group is introduced at the terminal of the bound silane coupling group.

The gels were immersed in 1 mg/ml of a (glucose oxidase/ phosphate buffer solution having pH 7.0). The reaction was carried out at 25° C. for about 30 minutes firstly under reduced pressure while mildly stirring and then for 60 minutes under atmospheric pressure while mildly stirring to effect immobilization. By this treatment, the amino group of glucose oxidase takes part in the reaction and forms an additional Schiff's base together with the aldehyde group of the carriers (gels). Thus, the glucose oxidase-immobilized gels (bioreactors) of the present invention were obtained, respectively.

Activity Test

The bioreactor of 200 mesh from the beads-like bioreactors described above insert was subjected to an activity test with respect to the degree of immobilization, for the purpose of comparison with the prior art bioreactor. Firstly, 10 ml of a 1 wt. % β-D-glucose solution (0.1M, pH 7.0, phosphate buffer solution) was carefully poured into a beaker containing 1 g of the aforesaid immobilized glass beads of the present invention. The mixture was mildly stirred for about 15 minutes to cause a reaction. From the reaction mixture, 9 ml was removed and 1 ml of a 5% potassium iodide solution was added thereto. By this treatment, $I^-$ was oxidized to $I_2$ (aq) by hydrogen peroxide released in the enzyme reaction. This $I_2$ was reduced by the voltametry method. By measuring the reduction wave, the $I_2$ content can be determined and thus, the degree of the enzyme immobilized in the bioreactor, i.e., the degree of activity, is determined.

The results obtained by the voltametry method of a conventional bioreactor obtained in a manner similar to the foregoing using the prior art glass as a carrier and the bioreactor of the present invention are shown in Table 1.

TABLE 1

| Carrier Used (beads) | Reduction Current* (mA) |
|---|---|
| Example | |
| Glass*like Gel | 0.7 |
| Comparative Example | |
| Commercially | 0.5 |

TABLE 1-continued

| Carrier Used (beads) | Reduction Current* (mA) |
|---|---|
| Available Glass | |

*0.53 VSNHE
The reduction current is obtained by subtracting a blank value.

The potential scanning speed is 20 mV/sec.

From the results above, it is understood that the bioreactor of the present invention provides obviously higher enzyme activity than the conventional bioreactor using the prior art glass as a carrier.

EXAMPLE 2

The bioreactor of the present invention was prepared in a manner similar to Example 1 except that the enzymes used were different.

The enzymes used and units of each of the enzymes used for immobilization per 1 mg of a carrier are shown in the table below

| Kind of Enzyme | Unit |
|---|---|
| Uricase | 0.25 u |
| Cholesterol Oxidase | 0.01 U |
| Acyl CoA Oxidase | 0.1 U |
| Urease | 1 U |
| Cholesterol Esterase | 0.03 U |
| Creatininase | 1 U |
| Acyl CoA Synthetase | 0.05 U |

EXAMPLE 3

Preparation of Fluorine-Substituted Glass-like Gel

A mixture (pH about 1) of 0.52 mol of tetraethoxysilane $Si(OC_2H_5)_4$, 1.72 mol of ethanol, 1.82 mol of water, 0.028 mol of hydrochloric acid was mixed for several ten minutes at room temperature with stirring until the system became homogeneous, followed by 0.058 to 0.115 mol of hydrogen fluoride was added with stirring.

Then the mixture was heated in a water bath of 80° C. for 3 days. By evaporating the ethanol formed during the hydrolysis and the remaining water hydrochloric acid and a trace amount of unreacted hydrogen fluoride, about 30 g of a glass-like gel was obtained.

Aminoalkylation

The thus obtained glass-like gel was ground to obtain beads of 120/200 mesh.

A 5 wt. % γ-aminopropyltriethoxysilane aqueous solution was adjusted to pH 3.5 with 5N hydrochloric acid. To 100 ml of the solution 5 g each of the aforesaid beads-like gel was added. Further the system was adjusted to pH 3.5. The mixture was charged in a four-necked flask equipped with a stirred, a thermometer and a Dimroth's funnel. While maintaining the temperature at 75° C. in a water bath, the reaction was carried out for 3 hours while vigorously stirring. After completion of the reaction, the beads were moved to a suction membrane filter to remove the unreacted γ-aminopropyltriethoxy silane with 1 l of distilled water. Then, the system was dried in a desicator to obtain three kinds of aminoalkylated glass-like gels having different grain sizes. The aminoalkylated gels are stored in a desicator.

Immobilization of Enzyme

The above-described aminoalkylated gels (bead-like) were immersed in each of a phosphate buffer solution (0.1M, pH 7.0) of bifunctional glutaraldehyde (2.5 wt. %). While reducing the pressure with an aspirator, the reaction was carried out for about 30 minutes with stirring. Subsequently, the reaction was carried out for about 30 minutes under normal pressure. The reaction temperature was 30° C. The reaction mixture was thoroughly washed with a phosphate buffer solution having pH 7.0 followed by drying. By this treatment, a Schiff's base containing an aldehyde group is introduced.

The gels were immersed in 10ml of a 1 mg/ml of a glucose oxidase/phosphate buffer solution having pH 7.0 (0.1M). The reaction was carried out at 25° C. for about 30 minutes firstly under reduced pressure while mildly stirring and then for 60 minutes under normal pressure while mildly stirring to effect immobilization. By this treatment, the amino group of glucose oxidase takes part in the reaction and forms an additional Schiff's base together with the aldehyde group of the carriers (gels). Thus, the glucose oxidase-immobilized glass-like gels (immobilized enzymes) of the present invention were obtained, respectively.

Figure 1:
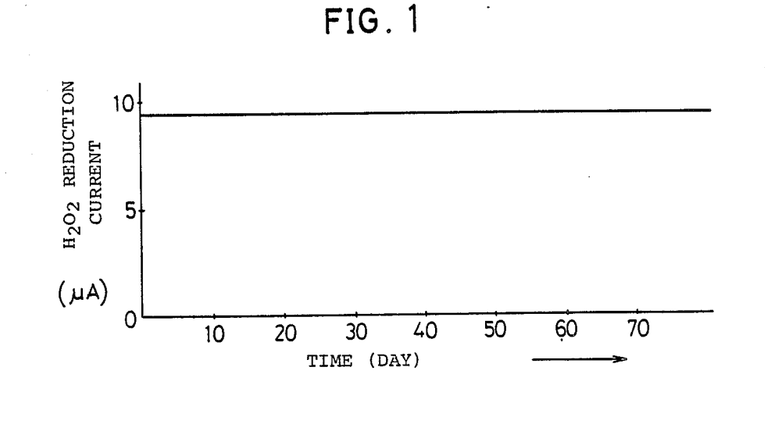
FIG. 1 is a graph illustrating the activity of an immobilized enzyme of this invention with the passage of time.

The thus obtained immobilized enzyme was examined with respect to activity with the passage of time by means of polarography. The results are shown in FIG. 1, wherein the measurement conditions are as follows:
Test Solution: $\beta$-D(+)-glucose, 300 mg/dl of 0.1M, pH 7.0 phosphate buffer
Measurement Temperature: 28° C.
Storage Temperature: 4° C.

The measurement was performed by means of polarography using a dropping mercury electrode, after mixing 1g of the immobilized enzyme with 11 ml of the test solution for 5 minutes with stirring and separating 10 ml of the mixture by filtration using a membrane filter. The half wave potential of $H_2O_2$ generated by the enzyme reaction was made $-0.85$ V (vs) Ag/AgCl electrode.

No change was observed in the activity even after 2 and one half months.

Figure 2:
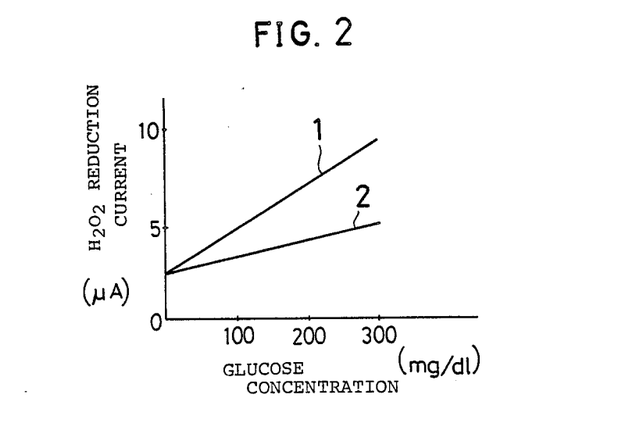
FIG. 2 is a graph illustrating the activity of an immobilized enzyme of this invention together with that of a comparative example.

On the other hand, an immobilized enzyme was obtained in a similar manner using a glass-like gel prepared in a similar manner but without using hydrogen fluoride. Comparison was made with the thus obtained immobilized enzyme. The results are shown in FIG. 2, within (1) indicates the example and (2) indicates a comparative example. As in shown FIG. 2, it is understood that the above-described immobilized enzyme is of about 2.5 times more active than the immobilized enzyme in which no fluorine atom has been introduce.

EXAMPLE 4

Glass-like gels were obtained in a manner similar to Example 3, except that the reaction was carried out under conditions wherein mole ratios of $HF/Si(OC_2H_5)_4$ were in the range of 0.1 to 0.5. To each of these carriers, glucose oxidase was immobilized in a manner similar to the foregoing to obtain immobilized enzymes. The relationship between the activities of these immobilized enzymes and the mole ratios described above is shown in FIG. 3. The measurement of the activities was also performed as described above.

Figure 3:
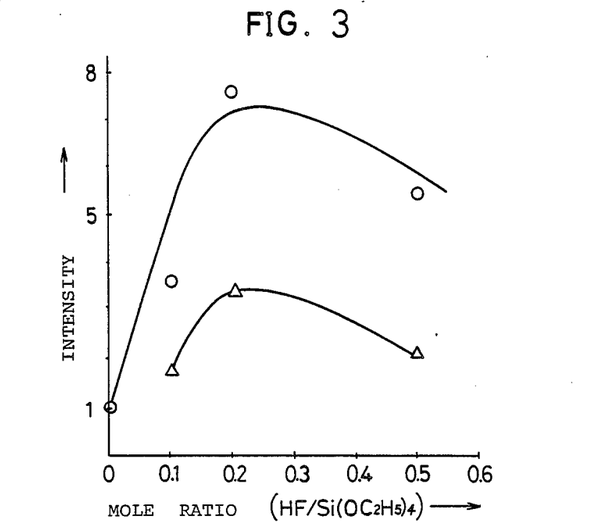
FIG. 3 is a graph illustrating the relationship between the relative activities and the mole ratios of $HF/Si(OC_2H_5)_4$ of immobilized enzymes of this invention.

As shown in figure, it is understood that the enzyme activity is affected by the content of hydrogen used in preparing the carriers and in particular, the maximum activity (about 7 times that of a blank test) appears at about 0.2 in the mole ratio. It is also understood that the addition of inorganic acids such as hydrochloric acid, etc. in the preparation of the carriers (plot O) is more suitable than no addition (plot $\Delta$).

Further SEM (Scanning Electron Microscope) ($\times 20000$) of the glass-like gels obtained in the mole ratios of 0.1 and 0.5 indicate that the porosity at the surfaces is higher than that of the system to which no fluorine has been introduced.

Figure 4:
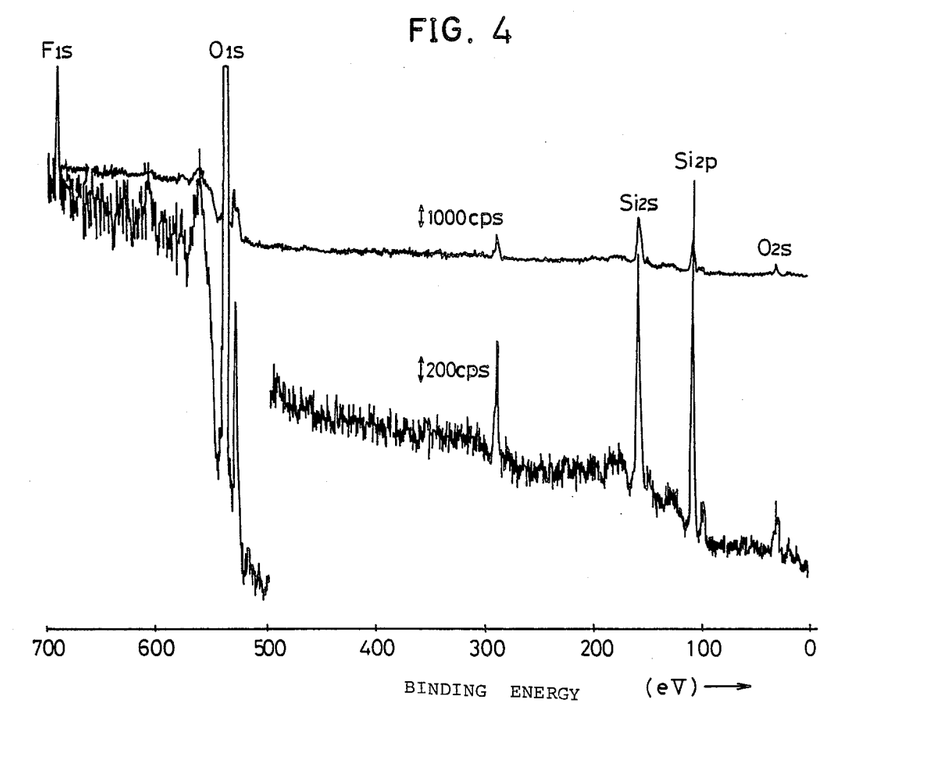
FIG. 4 is a graph illustrating the analytical chart with ESCA of a glass-like gel obtained in Example 4.

Further, an analytical chart of each of the porous glass-like gel carriers (glass beads-like) obtained in Example 4 by ESCA (Electron Spectrometry for Chemical Analysis or x ray photoelectron analysis) is shown in FIG. 4, where A represents a scanning speed of 2 eV/sec and B represents a scanning speed of 1 eV/sec. The conditions for the measurement of ESCA are as follows:
Target: Mg
Accelerated Potential: 8 kV
Filament: 30 mA
Ar Etching Conditions: accelerated potential 2 kV emission 30 mA time 15 minutes Because that the peak due to fluorine atoms is observed at a binding energy of about 700 eV, it is understood that the fluorine atoms are chemically bound. Further, Table 2 contains a comparison between a bulk state and a powder state with respect to the specific intensity of the peaks of $F_{1s}$ and $Si_{2s}$ in the ESCA spectrum of the carriers when $HF/Si(OC_2H_5)_4$ was 0.1 in a mole ratio. From the fact that the specific intensities of both are approximate to each other, it is understood that not only the surface but also the whole of the carriers is converted into a fluorine compound.

TABLE 2

| Carrier Sample | Specific Intensity of $F_{1s}/Si_{2s}$ |
|---|---|
| Bulk State | 0.36 |
| Powder State | 0.47 |

EXAMPLE 5

1 mole of tetraethoxysilane, 3,557 mols of ethanol, 3.759 mols of water and 0.28 mol of hydrochloric acid were mixed in turn and the mixture was vigorously stirred to obtain a homogeneous sol. The resulting sol was mixed with 0.2 mol of hydrogen fluoride and a solid glass-like gel was obtained in a manner similar to Example 3.

The effect of heat treatments at 300° C. and 500° C. on the gel were examined. That is 500 mg each of the carrier ground to a 120/200 mesh was heated at 300° C. and 500° C., respectively, in an electric furnace. Thereafter, aminoalkylation and immobilization of glucose oxidase were performed as in Example 3. The rate of immobilization (which was obtained by determining the protein contents in an enzyme solution prior to the immobilization and in an enzyme solution after the immobilization by the Lowry method and subtracting the difference in both) of each of the thus obtained immobilized enzymes was measured.

The results are shown in Table 3, together with comparative examples.

TABLE 3

| Carrier | Carrier treated with no hydrogen flouride | Carrier without heat treatment | Carrier heated at 300° C. | Carrier heated at 500° C. |
|---|---|---|---|---|
| Ratio of Immobilization (%) | 18 | 95 | 90 | 45 |

Figure 5:
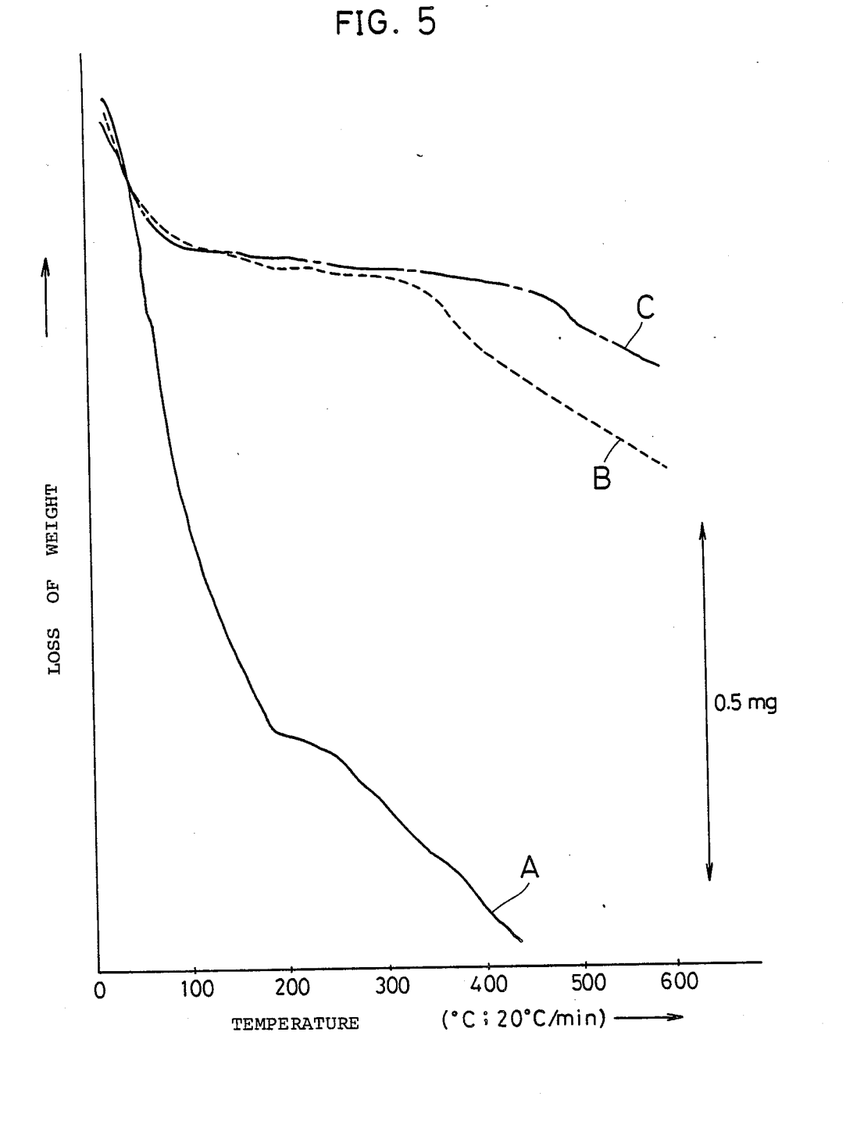
FIG. 5 is a graph illustrating the analytical chart with TG of glass-like gels obtained in Example 5.
Figure 6:
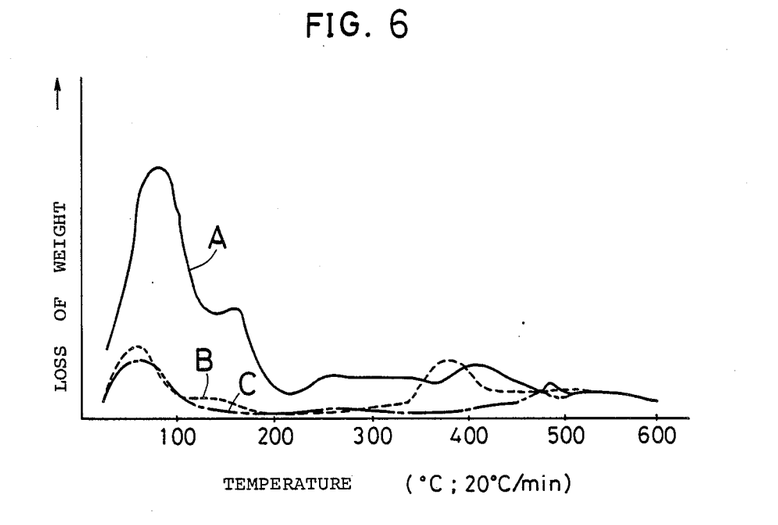
FIG. 6 is a graph illustrating the analytical chart with DTG of glass-like gels obtained in Example 5.

On the other hand, thermal weight analysis (TG) and differential thermal weight analysis A (DTG) were performed with each of the carriers prior to the aminoalkylation and the immobilization (carrier treated with no hyrogen fluoride . . . (A), carrier with no heat treatment . . . (B), carrier heat treated at 300° C. . . . (C)). The results are shown in FIG. 5 and FIG. 6, respectively.

As shown in the figures, it is understood that the silanol groups of the carrier treated with hydrogen fluoride are little changed to siloxane bonds with the heat treatment at about 300° C. and a moisture content absorbed by the carrier treated with hydrogen fluoride is extremely small.

EXAMPLE 6

To 1 mol of tetraethoxysilane $Si(OC_2H_5)_4$, 3.8 mols of water, 3.6 mols of ethylalcohol and 0.28 mol of hydrochloric acid were in turn added and the mixture was vigorously stirred to obtain a solution of tetraethoxysilane in an aqueous solvent. While stirring, 0.1 to 1.0 mol of hydrogen fluoride was added to the solution. The mixture was added at once to 5000 ml of fluid paraffin previously heated to about 80° C. The mixture was stirred to disperse the above described solution therein. The dispersed particles were gelled in about 30 minutes to obtain micro-spherical glass-like gel in a dispersed state.

Figure 7:
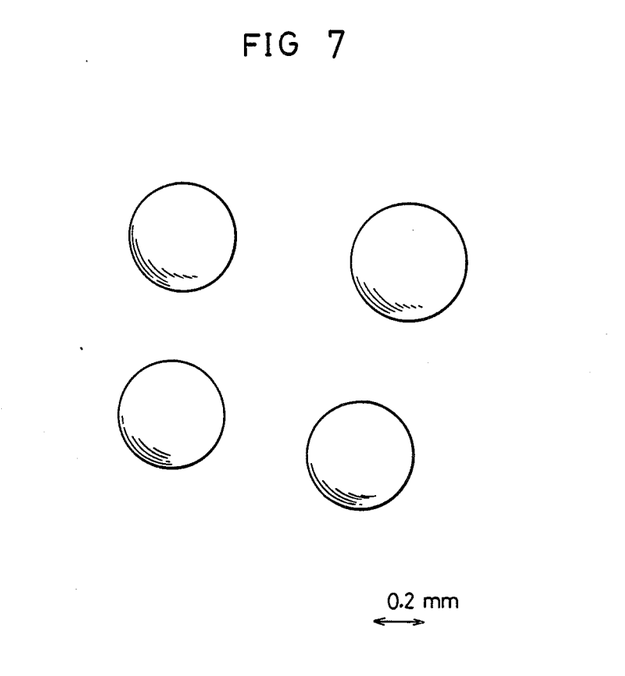
FIG. 7 is an enlarged perspective view of a glass-like gel obtained in Example 6.

The spherical glass-like gel described above was filtered using a membrane filter to separate from the medium. After the glass-like gel was repeatedly washed with acetone, the gel was dried at 100° C. The spherical glass-like gel was a uniform spherical form as shown in FIG. 7, almost more than 95% of which were relatively uniform in a pore diameter of about 250 to about 500 μm.

The glass-like gel was treated in a manner similar to Example 3 to obtain a micro-spherical, immobilized enzyme.

EXAMPLE 7

The bioreactors were prepared in a manner similar to Example 3 except that different enzymes were employed. The enzymes employed and the units of each of the enzymes used for immobilization per 1 mg of carrier are shown below.

| Kind of Enzyme | Unit (per 1 mg) |
| --- | --- |
| Cholesterol Oxidase | 0.01 U |
| Acyl CoA oxidase | 0.1 U |
| 3α-Hydroxysteroid Dehydrogenase | 0.05 U |
| Glucose-6-phosphate Dehydrogenase | 1 U |
| Glutamate-1-Dehydrogenase | 10 U |
| Peroxidase | 15 U |
| Hexokinase | 2 U |
| Urease | 1 U |
| Cholesterol Esterase | 0.03 U |
| Acyl CoA Synthetase (Co—Immobilization) | 0.05 U |
| Hexokinase/Glucose-6-phosphate Dehydrogenase | 2 U/1 U |

EXAMPLE 8

The bead-like, urease-immobilized enzyme and glutamate-1-dehydrogenase-immobilized enzyme obtained in Example 7 were filled up in a stainless tube having an inner diameter of 2 mm and a length of 5 cm, respectively. These immobilized enzyme columns were connected in series to perform an assay for urea.

The conditions of the assay are shown below the relative activities of the enzymes were measured varying the urea content. The results are shown in FIG. 8.

Mobile phase: solution of 0.1 mM NADPH and 0.83 mM 2-oxoglutarate
Flow rate: 1.09 ml/m
Detector: fluorophotometer (excitation wavelength, 360 nm detection wavelength, 450 nm)

Figure 8:
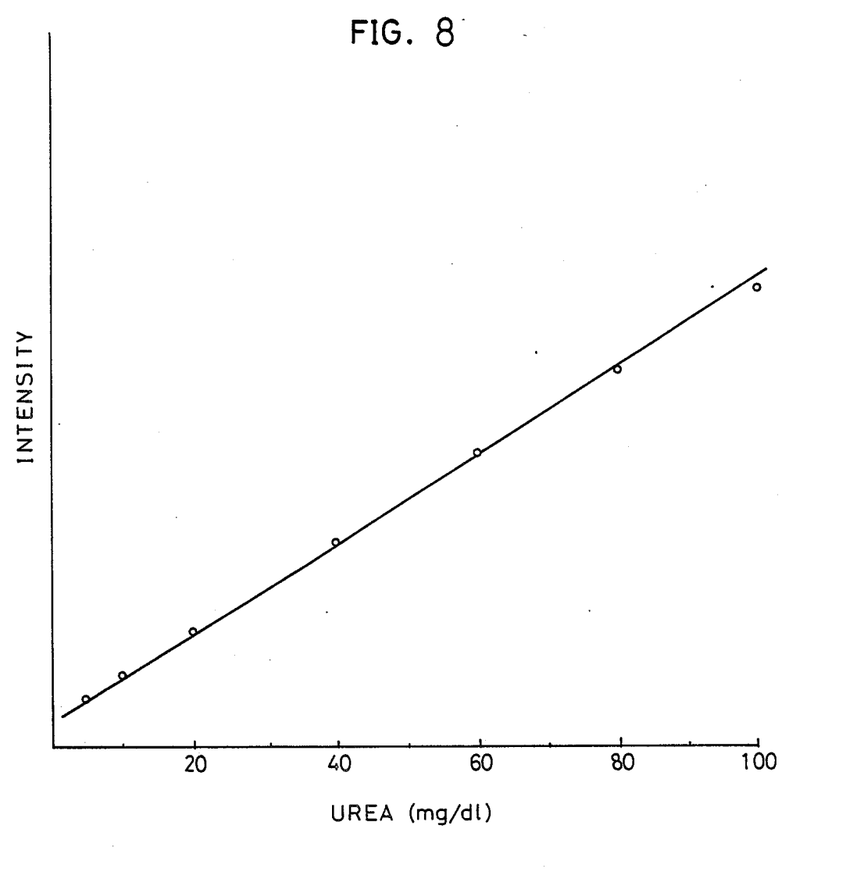
FIG. 8 is a graph illustrating the relative activity of the immobilized enzymes of Example 7.

As shown in FIG. 8, a good linear relationship was obtained between the urea content and the relative activity of the enzyme.

What we claim is:

1. A process for preparing a bioreactor, comprising the steps of:
   (a) hydrolyzing a metal alkoxide compound in an aqueous solvent containing from 0.05 to 1.0 mole of hydrogen fluoride per mole of the metal alkoxide, while evaporating off said solvent, to form a gel of the corresponding fluoride-substituted metal hydroxy compound gel,
   (b) treating said fluoride-substituted gel with a coupling agent, and
   (c) chemically bonding a peptide-containing compound to the treated gel to form said bioreactor.

2. The process of claim 1, wherein the hydrolysis is carried out in step (a) in an aqueous solvent containing a lower alcohol and 0.1–1.0 mole of hydrogen fluoride per mole of the metal alkoxide.

3. The process of claim 1, wherein the metal alkoxide is $Si(OCH_3)_4$ or $Si(OC_2H_5)_4$, and said alkoxide is hydrolyzed at a pH of 1–3 and a temperature between ambient temperature and 100° C.

4. The process of claim 3, wherein the hydrolysis is carried out in step (a) in an aqueous solvent containing a lower alcohol and 0.1–1.0 mole of hydrogen fluoride per mole of the metal alkoxide.

5. The bioreactor produced by the process of claim 2.

6. The biorecator produced by the process of claim 4.

7. A process for preparing a bioreactor comprising the steps of:
   (a) forming an aqueous mixture of a metal alkoxide compound with a lower alcohol and 0.1–1.0 mole of hydrogen fluoride per mole of the metal alkoxide;
   (b) hydrolyzing the mixture by dispersing the resulting metal alkoxide-hydrofluoric acid aqueous solution in a hot liquid medium to form a gel while evaporating of water and lower alcohol;
   (c) treating said gel with a coupling agent; and
   (d) immobilizing a peptide-containing compound by chemical bonds to said coupling agent treated gel.

8. The process of claim 7, in which the temperature of the liquid medium is 50 to 200° C.

9. The bioreactor produced by the process of claim 7.

10. The bioreactor produced by the process of claim 8.

* * * * *